United States Patent [19]

Duperret et al.

[11] Patent Number: 5,695,485

[45] Date of Patent: Dec. 9, 1997

[54] MALE CONTINENCE POUCH AND SHIELD

[76] Inventors: Ruth M. Duperret, 2755 W. Anklam Rd.#E, Tucson, Ariz. 85745; Corinne D. King, 874 W. Belltower Dr.; Montice King, 874 Belltower Dr., both of Green Valley, Ariz. 85614

[21] Appl. No.: 687,755

[22] Filed: Jul. 26, 1996

[51] Int. Cl.⁶ ..................................................... A61F 5/44
[52] U.S. Cl. .................................... 604/349; 604/352
[58] Field of Search ................................ 604/349–353

[56] References Cited

U.S. PATENT DOCUMENTS

| | | | |
|---|---|---|---|
| 2,699,782 | 1/1955 | Chester | 604/353 |
| 2,976,869 | 3/1961 | Silverstone | 604/353 |
| 4,197,849 | 4/1980 | Bostick | 604/352 |
| 4,886,509 | 12/1989 | Mattson | 604/349 |
| 5,342,332 | 8/1994 | Wheeler | 604/349 |
| 5,409,474 | 4/1995 | Fleeman-Hardwick | 604/352 |

*Primary Examiner*—Robert A. Clarke

[57] ABSTRACT

A disposable, male incontinence device which incorporates a number of improvements over prior art and which allows for ease of applying and removing in a sitting, standing, or prone position either by the user himself, or by an attendant. This device, which accommodates both dribbling and total incontinence, includes a waterproof outer layer, a highly absorbent middle layer, and an inner layer of permeable, non-absorbent material to protect the wearer's penis from moisture.

1 Claim, 2 Drawing Sheets

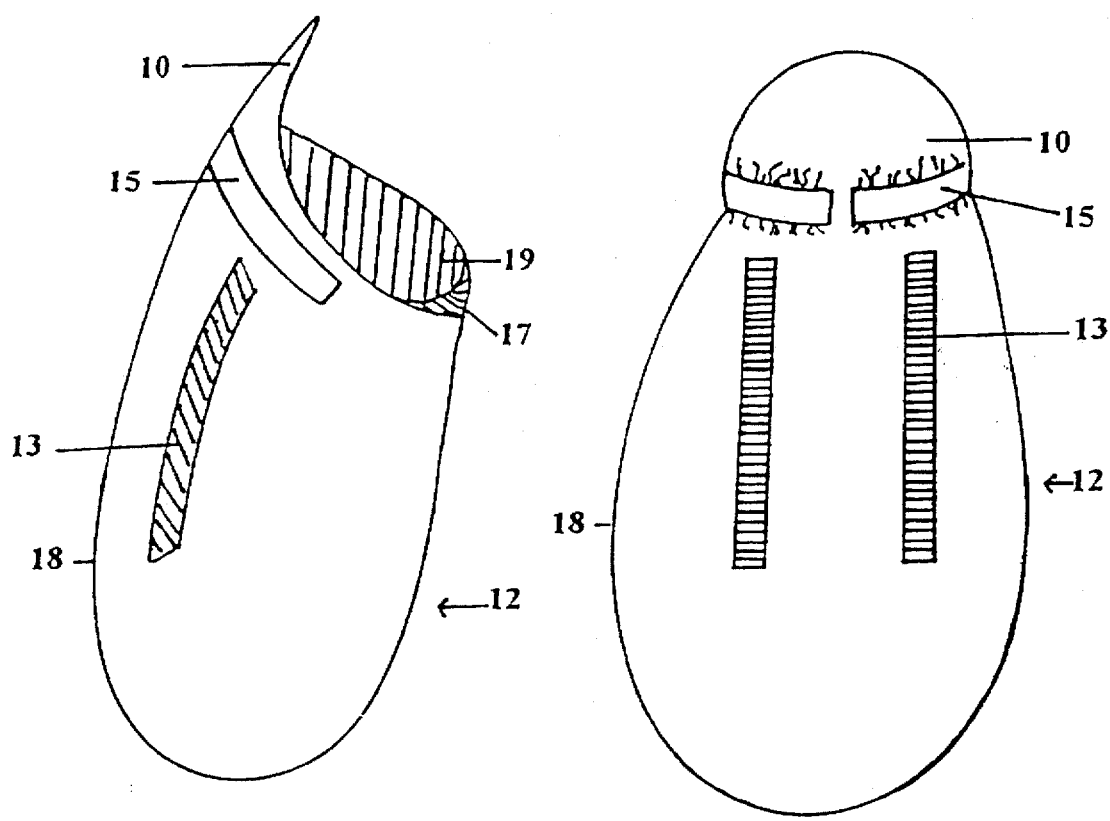

MALE CONTINENCE POUCH AND SHIELD

BACKGROUND

This invention is related to continence control problems, and more particularly to male continence problems.

Due to motorcycle accidents, auto accidents, swimming and other sports accidents, as well as a number of medical conditions, young men experience continence problems. This may take the form of continual dribbling of urine from the penis, or may take the form of uncontrollable excretion of two hundred cubic centimeters or more of urine at a given time. In addition, older males frequently experience either or both types of urinary incontinence, due to the ageing process. This can be occasioned by prostate enlargement, prostate surgery, dementia such as Alzheimer's disease, as well as by a host of other medical problems.

In a hospital setting, a Texas or Foley Catheter is sometime used to deal with incontinence, but in either of these cases there is an enhanced likelihood of infection and/or excoriation of the penis. Research has shown that the prolonged use of indwelling catheters occasions a marked decrease in life expectancy, as compared with males with similar conditions who do not use indwelling catheters.

In hospitals and nursing homes, a commonly used alternative to the indwelling catheter is the use of disposable diapers, similar to those used for infants. These are cumbersome and embarrassing to males of all ages. In addition, they make noise when the individual moves about. In any setting, the adult diapers are cannot be changed when the male is in a seated position. The male must be able to stand or be put to bed.

For the younger man caring for himself at home, at the work place, or in an educational setting, the adult diaper hampers mobility, and is embarrassing. The adult diaper is difficult or impossible to change for many young men who are paralyzed from the waist down, unless assistance is available.

Yet a third type of device is available. This is the incontinence guard similar to the sanitary napkin as worn by women. This frequently takes the shape of a triangular device which is wide at the top and narrow at the bottom. This device tends to deal only with a dribbling problem, and tends to be unsatisfactory to males of all ages, although less so for very elderly males suffering from dementia. This device allows the anterior pelvic area as well as the genitals and perineal areas to be wet intermittently or continually. Many males are embarrassed to use this device.

Although a number of male incontinent devices have been designed, there is as yet not a suitable product for general incontinence other than the adult diaper. There is a significant need for an effective continence treatment, yet one which will allow mobility in a variety of life situations. Prior art has followed several approaches to deal with the problem. None has been successful due to the various devices being bulky, inconveniently messy, difficult to use, exposing too much skin to wetness, putting stress on the ligaments which connect the penis to the body, requiring an embarrassing protrusion from the pelvic area, requiring adhesives irritating to the skin in order to hold the device in place, requiring rigid parts which are uncomfortable and/or dangerous to the male, or which deals only with mild dribbling rather than with heavy incontinence. An additional difficulty with any device dealing with incontinence, other than a diaper, is that the male penis involuntarily changes dimensions throughout the day and night, as a function of temperature, hormonal fluctuations, and the state of mind of the male. Older males frequently have a retracted penis, which in many cases virtually disappears into the body for extended periods of time. These are problems which must be addressed. Prior art consists of such devices as the following:

Seidel, U.S. Pat. No. 741,173, a urinal attached to a belt.
Morrow, U.S. Pat. No. 2,864,369 and Benovic, U.S. Pat. No. 3,035,579, urine bags with liners.
Garfinkel, U.S. Pat. No. 3,616,789, an incontinent garment.
Sanford, U.S. Pat. No. 3,707,969, a diaper type device.
Runeman, U.S. Pat. No. 4,710,188, a bag which receives the penis and scrotum.
Dahlgren, U.S. Pat. No. 4,901,375, a pouch holding a plastic urinal bottle.
Bryant, U.S. Pat. No. 5,074,853, a penis diaper which encloses the base of the penis with an elastic band in order to keep the device from falling off.
Grizzaffi, U.S. Pat. No. 5,275,592, an athletic supporter attached to a pouch which consists of a protruding rigid top part and a flaccid bottom part. The devise is partially supported by adhesives to the skin of the wearer.

The above cited devices utilize either a rigid urinal or a disposable diaper type material for absorbancy.

None of the above devices succeed in solving the problem of providing a convenient, unobtrusive, non-embarrassing device capable of keeping the male's skin dry, while dealing with the difficult problem of the constantly changing dimensions of the penis and its often retracted state, and which can handle the total urinary incontinence for a male, not merely a dribbling problem, which is small, discreet, and non protruding, which can be readily changed by the wearer or by a care giver while the wearer is sitting in a chair, which does not require irritating adhesives to the body, and which is flexible and comfortable. A suitable device must be simple, comfortable, and inexpensive, and must be effective whether dealing with a major or a minor incontinence problem, either of which is devastating to a male who must live with it.

SUMMARY OF THE INVENTION

The present invention creates a pouch rendered waterproof by an outer impermeable membrane, a middle layer of highly absorbent cellulose (polyethylene fibers with sodium polyacrylate or similar materials), and an inner layer next to the penis of a permeable, non-absorbent membrane of soft cellulose material. The pouch is made adjustable by means of adjustable tabs at the open end of the pouch. The absorbancy of the pouch is enhanced by multiple layers of the highly absorbable cellulose material at the closed end of the pouch, which material is capable of absorbing three hundred cubic centimeters of liquid. The penis of the male is channeled into the pouch by means of a padded dip in that side of the pouch which is next to the pelvic area of the wearer. The side of the pouch distal to the wearer has a raised shield rising from the pouch itself, and consisting of the three said layers of material. Such arrangement of the shield and the padded dip in the pouch take into account the changing dimension as well as the frequently retracted state of the penis, with the padded dip continuing to channel the penis into the pouch as the penis changes shape, and with the shield portion of the pouch containing and wicking into the pouch any moisture excreted outward from the body of the wearer by a retracted penis.

The pouch is held in place by means of adhesive strips attaching the pouch to the ordinary underwear briefs of the wearer. Thus, any excoriation of the skin of the abdomen of the wearer is obviated, as no adhesive material in required to be fixed upon the skin.

Being a small pouch, preferably about four and one-half inches long, and three and one-half inch wide, the pouch is accessible at the from of underwear briefs by the male himself. In the same way, a care giver can conveniently change the device, with a minimum of undressing and inconvenience to the wearer. Further, being light in weight and small in compass, an additional supply may be easily carried and easily disposed.

This invention is equally useful whether there is a major or minor continence problem, by means of the multiple cellulose layer at the lower part of the pouch, sufficiently commodious to contain three hundred cubic centimeters of liquid.

This invention is both compact and light in weight, by means of its construction of absorbed cellulose and light weight membranes. Therefore, both bulkiness and protrusion from the pelvic area are eliminated. The invention is thereby made useful to males of all ages who have a loss of bladder control, such as the young man living with paralysis, the older man with a problem following prostate surgery, the medical facility resident suffering from Alzheimer's disease or other dementias, and the male of any age with a handicapped condition where continence is a problem.

Inconvenient messiness and difficulty of use are eliminated by means of the device's accessibility, total containment of liquid, and ease of disposal.

This device places no stress upon the ligaments which connect the penis to the body, as none of the weight of the pouch is supported by penis. This support is accomplished by means of using the adhesive strips which attach the pouch to the briefs of the wearer.

The skin of the male is kept dry at all times, by means of the highly adsorbent material within the pouch, by means of the inner permeable non-absorbed liner, and by means of the channel and shield which direct the stream of urine into the pouch and wick the liquid into the adsorbent material. Only the penis is contained within the pouch, and the penis is protected from contact with moisture by the permeable, non-absorbent membrane.

BRIEF DESCRIPTION OF THE DRAWINGS

FIG. 2 is a side view of the device.

FIG. 3 is a frontal view depicting the tabs adjusted to tighten around the base of the wearer's penis.

DETAILED DESCRIPTION OF THE PREFERRED EMBODIMENT

Figure 1:
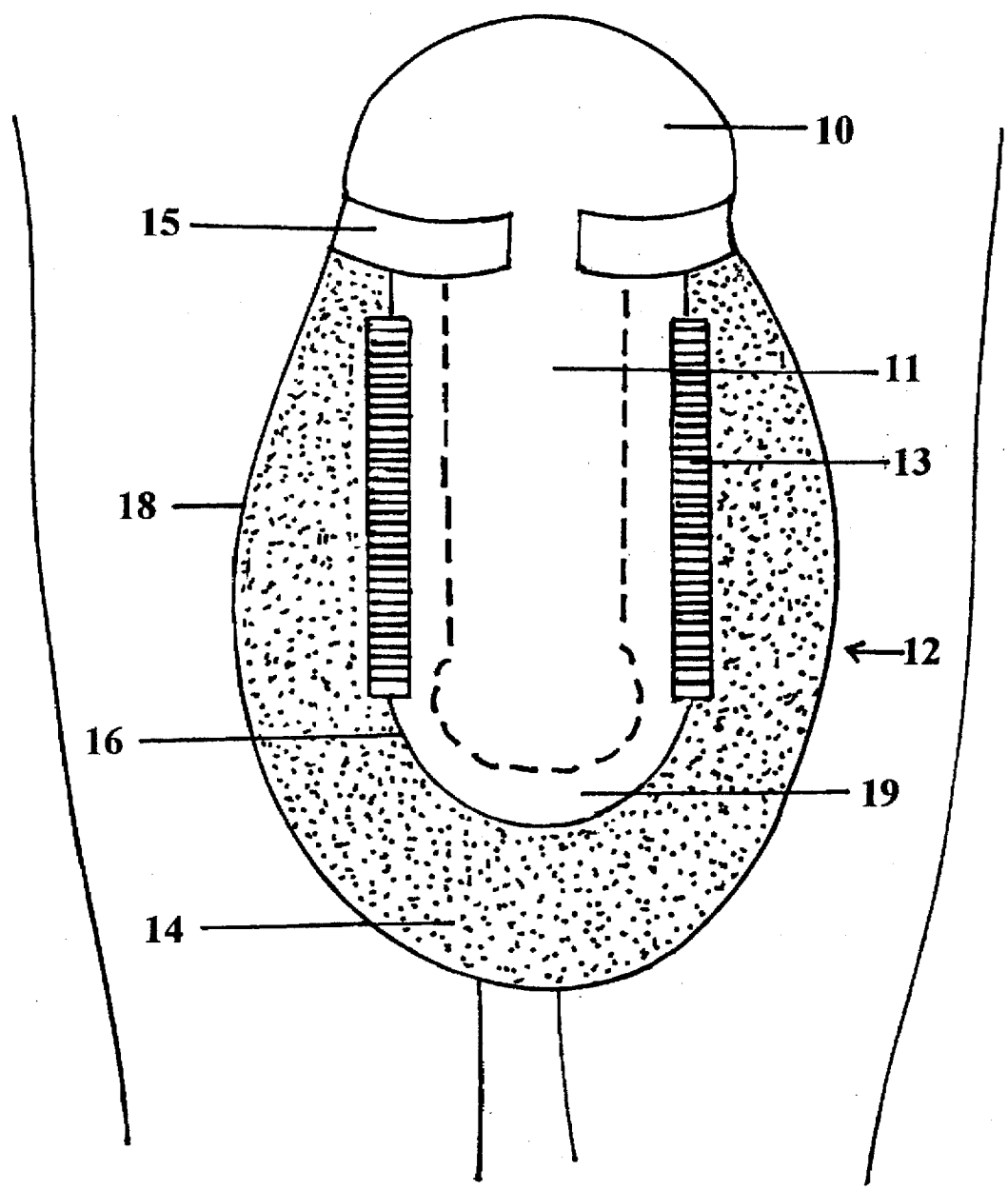
FIG. 1 is a frontal view of the device in use.

FIG. 1, is a frontal view of the pouch 12. Pouch 12 is positioned to accept penis 11 into penis receiving cavity 19. The shield 10 rises from the pouch to a height just above the base of the penis. Adhesive strips 13 attach the pouch to the underwear brief, not shown. Multiple layers of absorbent material 14, made of hydrophillic substances, line the area of the pouch enclosed in the outer impermeable layer 18 and the interior, permeable, non-absorbent layer 16. Tabs 15 allow the wearer to adjust the upper end of the pouch around the base of the penis to ensure a snug fit.

FIG. 2, is a side view of the device depicting semicircular shield 10 rising from the body of the pouch 12. A padded channel 17 directs the penis into the receiving cavity 19. Adhesive strip 13 attaches the pouch to the underwear briefs, not shown. Adjustable tab 15 adjusts the size of the opening of the pouch.

FIG. 3, is a frontal view of the pouch 12 illustrating adjustable tabs 15 pulled taunt to allow the user to adjust the size of the opening of the pouch.

We claim:

1. A device for major and minor male incontinence comprising a disposable pouch, having:

a) an open end;

b) a closed end;

c) a front side adapted to be placed distal to the male wearer of the pouch;

d) a back side adapted to be placed proximal to the male wearer of the pouch;

e) a substantially flattened cylindrical shape, and a size suitable for receiving the male wearer's penis;

f) an integral padded penis channel near the open end of the pouch, and situated on the back side of the pouch;

g) an integral semicircular shield at the open end of the pouch, and situated on the front on the front side of the pouch;

h) an exterior layer composed of an impermeable membrane;

I) an interior layer composed of a permeable, non-absorbent membrane;

j) a layer of material between the two membranes, and composed of hydrophilic substances;

k) multiple layers of said hydrophilic substances being within the closed end of the pouch;

l) adhesive stripes located on the front side of the pouch; and m) adjustable tabs located just below the open end of the pouch and on the back side of the pouch.

* * * * *